US010258244B2

United States Patent
Sharma et al.

(10) Patent No.: US 10,258,244 B2
(45) Date of Patent: Apr. 16, 2019

(54) METHOD AND SYSTEM FOR MACHINE LEARNING BASED ASSESSMENT OF FRACTIONAL FLOW RESERVE

(71) Applicant: Siemens Healthcare GmbH, Erlangen (DE)

(72) Inventors: Puneet Sharma, Princeton Junction, NJ (US); Ali Kamen, Skillman, NJ (US); Bogdan Georgescu, Plainsboro, NJ (US); Frank Sauer, Princeton, NJ (US); Dorin Comaniciu, Princeton Junction, NJ (US); Yefeng Zheng, Princeton Junction, NJ (US); Hien Nguyen, Houston, TX (US); Vivek Kumar Singh, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/958,483

(22) Filed: Apr. 20, 2018

(65) Prior Publication Data
US 2018/0242857 A1 Aug. 30, 2018

Related U.S. Application Data

(63) Continuation of application No. 15/616,380, filed on Jun. 7, 2017, now Pat. No. 9,974,454, which is a (Continued)

(51) Int. Cl.
*A61B 5/026* (2006.01)
*A61B 5/00* (2006.01)
(Continued)

(52) U.S. Cl.
CPC ............ *A61B 5/026* (2013.01); *A61B 5/0261* (2013.01); *A61B 5/0263* (2013.01);
(Continued)

(58) Field of Classification Search
CPC ..... A61B 5/026; A61B 5/0261; A61B 5/0263; A61B 5/7264; A61B 5/7267;
(Continued)

(56) References Cited

U.S. PATENT DOCUMENTS 6,236,878 B1 5/2001 Taylor et al.
6,471,656 B1 10/2002 Shalman et al.
(Continued)

FOREIGN PATENT DOCUMENTS

CN 1864646 A 11/2006
CN 1911174 A 2/2007
(Continued)

OTHER PUBLICATIONS

C.A. Taylor, et al., "Open Problems in Computational Vascular Biomechanics: Hemodynamics and Arterial Wall Mechanics," Comput Methods Appl Mech. Eng., vol. 198, pp. 3514-3523, 2009.
(Continued)

*Primary Examiner* — Bo Joseph Peng

(57) ABSTRACT

A method and system for determining fractional flow reserve (FFR) for a coronary artery stenosis of a patient is disclosed. In one embodiment, medical image data of the patient including the stenosis is received, a set of features for the stenosis is extracted from the medical image data of the patient, and an FFR value for the stenosis is determined based on the extracted set of features using a trained machine-learning based mapping. In another embodiment, a medical image of the patient including the stenosis of interest is received, image patches corresponding to the stenosis of interest and a coronary tree of the patient are detected, an FFR value for the stenosis of interest is determined using a trained deep neural network regressor applied directly to the detected image patches.

30 Claims, 12 Drawing Sheets

Related U.S. Application Data continuation of application No. 14/516,163, filed on Oct. 16, 2014, now Pat. No. 9,700,219.

(60) Provisional application No. 61/891,920, filed on Oct. 17, 2013.

(51) Int. Cl.

| | | |
|---|---|---|
| *A61B 6/03* | (2006.01) | |
| *A61B 6/00* | (2006.01) | |
| *A61B 8/06* | (2006.01) | |
| *G06T 7/00* | (2017.01) | |
| *G06K 9/62* | (2006.01) | |
| *G06K 9/46* | (2006.01) | |
| *G06T 7/20* | (2017.01) | |
| *G16H 50/30* | (2018.01) | |
| *G16H 50/50* | (2018.01) | |
| *G16H 50/20* | (2018.01) | |
| *A61B 8/12* | (2006.01) | |
| *A61B 8/08* | (2006.01) | |
| *A61B 8/00* | (2006.01) | |

(52) U.S. Cl.
CPC .......... *A61B 5/7264* (2013.01); *A61B 5/7267* (2013.01); *A61B 5/7282* (2013.01); *A61B 6/032* (2013.01); *A61B 6/504* (2013.01); *A61B 6/507* (2013.01); *A61B 6/5217* (2013.01); *A61B 8/06* (2013.01); *G06K 9/46* (2013.01); *G06K 9/6256* (2013.01); *G06T 7/0012* (2013.01); *G06T 7/0016* (2013.01); *G06T 7/20* (2013.01); *G16H 50/20* (2018.01); *G16H 50/30* (2018.01); *G16H 50/50* (2018.01); *A61B 6/563* (2013.01); *A61B 8/0891* (2013.01); *A61B 8/12* (2013.01); *A61B 8/5223* (2013.01); *A61B 8/565* (2013.01); *G06T 2207/10081* (2013.01); *G06T 2207/10088* (2013.01); *G06T 2207/10101* (2013.01); *G06T 2207/10132* (2013.01); *G06T 2207/20081* (2013.01); *G06T 2207/30048* (2013.01); *G06T 2207/30104* (2013.01); *G06T 2211/404* (2013.01)

(58) Field of Classification Search
CPC ....... A61B 5/7282; A61B 6/032; A61B 6/504; A61B 6/507; A61B 6/5217; A61B 6/563; A61B 8/06; A61B 8/0891; A61B 8/12; A61B 8/5223; A61B 8/565; G16H 50/50; G16H 50/30; G16H 50/20; G06K 9/46; G06K 9/6256; G06T 7/0012; G06T 7/0016; G06T 7/20; G06T 2207/10081; G06T 2207/10088; G06T 2207/10101; G06T 2207/10132; G06T 2207/20081; G06T 2207/30048; G06T 2207/30104; G06T 2211/404
See application file for complete search history.

(56) References Cited

U.S. PATENT DOCUMENTS

| | | |
|---|---|---|
| 7,796,796 B2 | 9/2010 | Camus |
| 7,860,290 B2 | 12/2010 | Gulsun et al. |
| 7,953,266 B2 | 5/2011 | Gulsun et al. |
| 8,098,918 B2 | 1/2012 | Zheng et al. |
| 8,157,742 B2 | 4/2012 | Taylor |
| 8,200,466 B2 | 6/2012 | Spilker et al. |
| 8,249,815 B2 | 8/2012 | Taylor |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| 8,386,188 B2 | 2/2013 | Taylor et al. |
| 8,700,552 B2 | 4/2014 | Yu et al. |
| 2004/0077952 A1 | 4/2004 | Rafter et al. |
| 2006/0239528 A1 | 10/2006 | Camus et al. |
| 2008/0085050 A1 | 4/2008 | Barbu |
| 2008/0292049 A1 | 11/2008 | Meissner |
| 2009/0292046 A1 | 11/2009 | Dorgan et al. |
| 2010/0017171 A1 | 1/2010 | Spilker et al. |
| 2010/0067760 A1 | 3/2010 | Zhang et al. |
| 2011/0224542 A1 | 9/2011 | Mittal et al. |
| 2012/0022843 A1 | 1/2012 | Ionasec et al. |
| 2012/0041301 A1 | 2/2012 | Redel |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1 | 3/2012 | Sharma et al. |
| 2012/0121151 A1 | 5/2012 | Bernhardt et al. |
| 2012/0150516 A1 | 6/2012 | Taylor et al. |
| 2012/0203530 A1 | 8/2012 | Sharma et al. |
| 2012/0232386 A1 | 9/2012 | Mansi |
| 2012/0243761 A1 | 9/2012 | Senzig et al. |
| 2013/0054214 A1 | 2/2013 | Taylor |
| 2013/0064438 A1 | 3/2013 | Taylor et al. |
| 2013/0138436 A1 | 5/2013 | Yu et al. |
| 2013/0138589 A1 | 5/2013 | Yu et al. |
| 2013/0246034 A1 | 9/2013 | Sharma et al. |
| 2014/0058715 A1 | 2/2014 | Sharma et al. |
| 2014/0072213 A1 | 3/2014 | Paiton |
| 2014/0073976 A1 | 3/2014 | Fonte et al. |
| 2014/0100451 A1 | 4/2014 | Tolkowsky |
| 2015/0112182 A1 | 4/2015 | Sharma et al. |
| 2015/0125049 A1 | 5/2015 | Taigman et al. |
| 2015/0161987 A1 | 6/2015 | Horesh et al. |
| 2015/0161988 A1 | 6/2015 | Dognin et al. |
| 2015/0170000 A1 | 6/2015 | Szegedy et al. |
| 2015/0238148 A1 | 8/2015 | Georgescu et al. |
| 2015/0245775 A1 | 9/2015 | Fonte et al. |

FOREIGN PATENT DOCUMENTS

| | | |
|---|---|---|
| EP | 3057510 | 8/2016 |
| EP | 3282381 A1 | 2/2018 |
| WO | 20140072861 A2 | 5/2014 |
| WO | 2015058044 | 4/2015 |

OTHER PUBLICATIONS

Chamuleau et al., "Association between coronary lesion severity and distal microvascular resistance in patients with coronary artery disease," Am J Physiol Heart Circ Physiol, vol. 285, pp. H2194-H2200, 2003.

De Bruyne et al., "Simultaneous Coronary Pressure and Flow Velocity Measurements in Humans," Circulation, vol. 94, pp. 1842-1849, 1996.

H. Vernon Anderson et al., "Coronary Atery Flow Velocity is Related to Lumen Area and Regional Left Ventricular Mass," Circulation, vol. 102, pp. 48-54, 2000.

Bengio et al., Unsupervised Feature Learning and Deep Learning: A Review and New Perspectives, Jun. 24, 2012, http://arxiv.org/abs/1206.5538v1, Note, it is Version 1.

Hau, "Fractional flow reserve and complex coronary pathologic conditions", European Heart Journal, 25:723-727 (2004).

Zhou et al., Shape Regression Machine, IPMI, LNCS 4584: 13-25 (2007).

(56) References Cited

OTHER PUBLICATIONS

Huo et al., "A Validated Predictive Model of Coronary Fractional Flow Reserve", JR. Soc. Interface,19 pages, Jun. 7, 2012.
Deng, "Three Classes of Deep Learning Architectures and Their Applications: A Tutorial Survey", APSIPA Transactions on Signal and Information Processing, 2012.
Krizhevsky et al., "ImageNet Classification with Deep Convolutional Neural Networks", Conference: Advances in Neural Information Processing Systems 25, 2012, pp. 1106-1114.
PCT International Search Report dated Jan. 28, 2015 corresponding to PCT International Application No. PCT/US2014/061063 filed Oct. 17, 2014 (10 Pages).
Gustavo Carneiro et al., "Multiple dynamic models for tracking the left vehicle of the heart from ultrasound data using particle filters and deep learning architectures", 2010 IEEE Conference on Computer Vision and Pattern Recognition (CVPR), San Francisco, CA, USA, IEEE, Piscataway, NJ, USA, 8 pages, XP031725842, ISBN: 978-1-4244-6984-0 / Jun. 13, 2010.
Zheng et al., "Four-Chamber Heart Modeling and Automatic Segmentation for 3D Cardiac CT Volumes Using Marginal Space Learning and Sleerable Features", IEEE Trans. on Medical Imaging, vol. 27, No. 11, pp. 1668-1681, 2008.
Ghesu et al., Marginal Space Deep Learning: Efficient Architecture for Detection in Volumetric Image Data, Medical Image Computing and Computer-Assisted Intervention—MICCAI 2015, vol. 9349 of the series Lecture Notes in Computer Science, 8 pages Nov. 18, 2015.
Ghesu et al., Marginal Space Deep Learning: Efficient Architecture for Detection in Volumetric Image Parsing, IEEE Transactions on Medical Imaging, vol. 35, No. 5, May 2016.
Chinese Office Action dated Jan. 22, 2019 in corresponding Chinese Application No. 201480069085.7.
Extended European Search Report (EESR) dated Feb. 12, 2019 in corresponding European Patent Application No. 18205438.7.
Bernhard Stefan et al: "Transient integral boundary layer method to calculate the translesional pressure drop and the fractional flow reserve in myocardial bridges", Biomedical Engineering Online, Biomed Central LTD, London, GB; vol. 5, No. 1, Jun. 21, 2006 (Jun. 21, 2006), p. 42, XP021018067; ISSN: 1475-925X, DOI:10.1186/1475-925X-5-42.

1. Initialization $t = 0$.
   (a) Set the fixed A and B (the normalization matrices), $\lambda$ (the regularization coefficient), and $\eta$ (the shrinkage factor).
   402 (b) Set the values related to the stopping criteria : $T_{max}$ (the maximum number of iterations) and $J_{min}$ (the minimum cost function).
   (c) Set initial values for $t = 0$: $g_0(x) = 0$ and $r_0(x) = y(x)$.

2. Iteration $t = 1, \ldots, T_{max}$
   404 (a) Find the optimal $\hat{h}_t$ using the feature selection algorithm in Figure 2.
   406 (b) Form the new function $g_t(x) = g_{t-1}(x) + \eta\hat{h}_t(x)$.
   408 (c) Evaluate the approximation error $r_t(x) = y(x) - g_t(x)$ and the cost function $J(g_t)$.
   410 (d) Check convergence, e.g., see if $J(g_t) < J_{min}$.

FIG. 4

1. Initialization.
   - Create a random permutation of $\{1,2,...,q\}$, yielding $\{[1], [2],...,[q]\}$.
2. Interation over the dimension of the output variable $i = 1,2,...,q$
   - (optional) Sample $M'$ features from the dictionary set and form the reduced set of weak functions $H'$.
   - (optional) Sample $N'$ data points from the training set.
   - Loop over the feature $f_l = 1,2,...,M'$ to find $h_{[i]} = \arg\min_{f_l} J^{[i]}(f_l, \hat{w}_l(f_l))$.
   - Form the new vector $h^{[i]} = [h^{[i-1]T}, h_{[i]}]^T$.

FIG. 5

METHOD AND SYSTEM FOR MACHINE LEARNING BASED ASSESSMENT OF FRACTIONAL FLOW RESERVE

This application is a continuation of U.S. patent application Ser. No. 15/616,380, filed Jun. 7, 2017, which is a continuation of U.S. patent application Ser. No. 14/516,163, filed Oct. 16, 2014 and issued as U.S. Pat. No. 9,700,219, which claims the benefit of U.S. Provisional Application No. 61/891,920, filed Oct. 17, 2013, the disclosure of which is herein incorporated by reference.

BACKGROUND OF THE INVENTION

The present invention relates to non-invasive functional assessment of coronary artery stenosis, and more particularly, to machine learning based non-invasive functional assessment of coronary artery stenosis from medical image data.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. QCA only evaluates the morphological significance if the stenosis and has a number of other limitations. Pressure wire based FFR measurements involve risks associated with the intervention necessary to insert the pressure wire into the vessel, and for a very narrow stenosis, the pressure wire may induce an additional pressure drop.

Recently, mechanistic models have been proposed that use mathematical equations to model the physics of the blood flow in a three-dimensional anatomical model of the coronary vessels of a patient extracted from medical images. Such approaches rely on physics-based mathematical equations to model the physiology at rest and at hyperemia, thereby allowing one to numerically solve the equations on a computer and determine the flow and pressure drop for an individual patient. The most widely used physics-based model is the Navier-Stokes equation, which is a non-linear partial differential equation that is based on principles of mass, momentum, and energy conservation and is used to characterize the flow of blood in the coronary arteries. This is often coupled with mathematical equations that model the physiology of the upstream (heart, aorta) and downstream (myocardium) regions of the anatomy. Depending on the complexity and clinical use case, these methods can be used to incorporate physiological models at various scales. Although various types of physics-based models, boundary conditions, and physiological assumptions have been proposed for blood flow, a common theme of mechanistic models is their use of mathematical equations to model the various physiological interactions explicitly. However, a drawback of such mechanistic models is the high computational cost and complexity of associated with the model preparation and numerical solution of the physics-based equations. Additionally, such mechanistic models typically incorporate only anatomical and some partial physiological measurements, and leave out other meaningful measurements.

BRIEF SUMMARY OF THE INVENTION

The present disclosure provides methods and systems for machine learning based assessment of hemodynamic indices from medical image data. Embodiments of the present invention provide a data-driven, statistical methods to calculate one or more hemodynamic indices, such as fractional flow reserve (FFR), coronary flow reserve (CFR), instantaneous wave-free ratio (IFR), hyperemic stress reserve (HSR), basal stenosis resistance (BSR), and index of microcirculatory resistance (IMR), from input parameters including one or more of anatomical, functional, diagnostics, molecular, and demographic information from an individual patient, or directly from medical image data. Embodiments of the present invention employ machine-learning algorithms to learn the complex mapping between the input parameters or the input medical image data and the output hemodynamic index.

In one embodiment of the present invention, medical image data of the patient including the stenosis of interest is received. A set of features for the stenosis of interest is extracted from the medical image data of the patient. A FFR value for the stenosis of interest is determined based on the extracted set of features using a trained machine-learning based mapping.

In another embodiment of the present invention, a medical image of the patient including the stenosis of interest is received. Image patches corresponding to the stenosis of interest and a coronary tree of the patient are detected. An FFR value for the stenosis of interest is determined using a trained deep neural network regressor applied directly to the detected image patches.

These and other advantages of the invention will be apparent to those of ordinary skill in the art by reference to the following detailed description and the accompanying drawings.

BRIEF DESCRIPTION OF THE DRAWINGS

FIG. 4 illustrates an algorithm for training a machine-learning based mapping using enhanced image-based boosting ridge regression according to an embodiment of the present invention;

FIG. 5 illustrates a feature selection algorithm according to an embodiment of the present invention;

DETAILED DESCRIPTION

Figure 1:
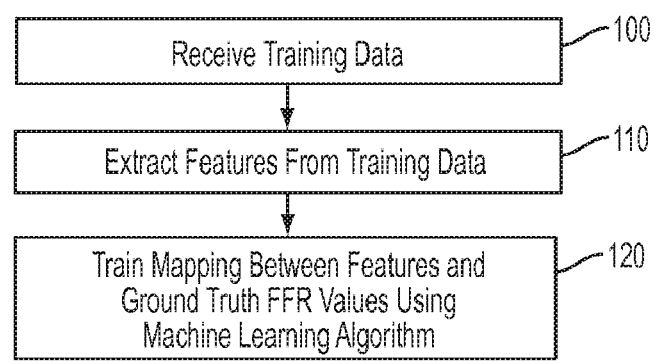
FIG. 1 illustrates a method of training a machine-learning based mapping for determining FFR according to an embodiment of the present invention.

The present invention relates to methods and systems for machine-learning based assessment of hemodynamic indices for coronary artery stenosis, such as fractional flow reserve (FFR). Embodiments of the present invention are described herein to give a visual understanding of method for assessing coronary artery stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Fractional Flow Reserve (FFR) is a functional measure for determining the hemodynamic significance of a coronary stenosis. FFR is defined as the fraction of the flow in the stenosed vessel to the flow in a normal vessel, both of which are determined at maximal hyperemia. In particular, FFR can be expressed as:

$$FFR = \frac{Q_{max}^{Stenosis}}{Q_{max}^{Normal}}. \quad (1)$$

Here, max refers to the maximal hyperemia condition. The Normal vessel is hypothetical (i.e., if the stenosis is not present). Since such as normal vessel is not present, an alternate pressure-based formulation is typically used for quantifying FFR. Due to the coronary auto-regulation mechanism, the resting flow remains constant in a range of perfusion pressures. Auto-regulation is achieved by lowering the microvascular resistance. In order to calculate FFR via pressure measurements, one needs to operate in the maximal hyperemia regime, where the pressure is directly proportional to the flow (since the myocardial resistance is now fixed at its lowest value and can change no further). As a result, flow-rate terms can be substituted by appropriate perfusion pressure terms, all of which can be measured in the stenosed vessel, with no need for the hypothetical normal vessel. In this case, FFR can be calculated as:

$$FFR = \frac{Q_{max}^{Stenosis}}{Q_{max}^{Normal}} = \frac{\Delta P^{Stenosis}}{\Delta P^{Normal}} = \frac{P_d - P_v}{P_{A_0} - P_v} = \frac{P_d}{P_{A_0}}. \quad (2)$$

Here, $P_d$ and $P_{A_0}$ are the average distal pressure and aortic pressure, respectively, over the cardiac cycle, and $P_v$ is the venous pressure ($P_v \approx 0$). FFR varies in the range [0, 1], with 0.80 typically being the cut-off value below which the stenosis is deemed hemodynamically significant (i.e., ischemic).

In addition to FFR, other hemodynamic indices, such as pressure-drop, coronary flow reserve (CFR), instantaneous wave-free ratio (IFR), hyperemic stress reserve (HSR), basal stenosis resistance (BSR), and index of microcirculatory resistance (IMR), can be used to assess coronary artery stenoses. Embodiments of the present invention are described herein as estimating FFR for a patient. It is to be understood that the present invention is not limited to FFR estimation and embodiments of the present invention may be similarly applied to estimate other hemodynamic indices, as well.

Embodiments of the present invention utilize a data-driven, statistical method to calculate one or more hemodynamic indices from anatomical, functional, diagnostic, molecular, and/or demographic information from an individual patient. Embodiments of the present invention employ machine-learning algorithms to learn the complex mapping between the input parameters (e.g., anatomical, function, and/or demographic information) and the output quantity of interest (e.g., FFR). Unlike mechanistic model based methods, embodiment of the present invention do not rely on an a priori assumed model describing the relationship between the inputs and the output. Instead, embodiments of the present invention determine the optimal mapping via a statistical approach using machine-learning algorithms to learn the mapping from training data.

According to an advantageous embodiment, a machine-learning based method for determining FFR includes two phases: a training phase and a prediction phase. The training phase is an offline process, during which a database of annotated training data with ground truth measurements is assembled. In particular, a database of lesions (stenoses) with invasively measured FFR values from multiple patients is constructed. In this database, each instance (i.e., an invasively measured FFR value) is represented by a number of features, such as anatomical functional, diagnostic, molecular, and/or demographic measurements. The training phase then learns or trains a mapping between the features and the ground truth values by minimizing the best fit between predictions and ground truth values over the entire training database.

The prediction phase is an online process, whereby an FFR value for a new dataset (unseen data) is calculated by using the learned mapping from the training phase. To achieve this, the required features are extracted from the new dataset and the values for the features are used as input to the pre-learned mapping.

Figure 2:
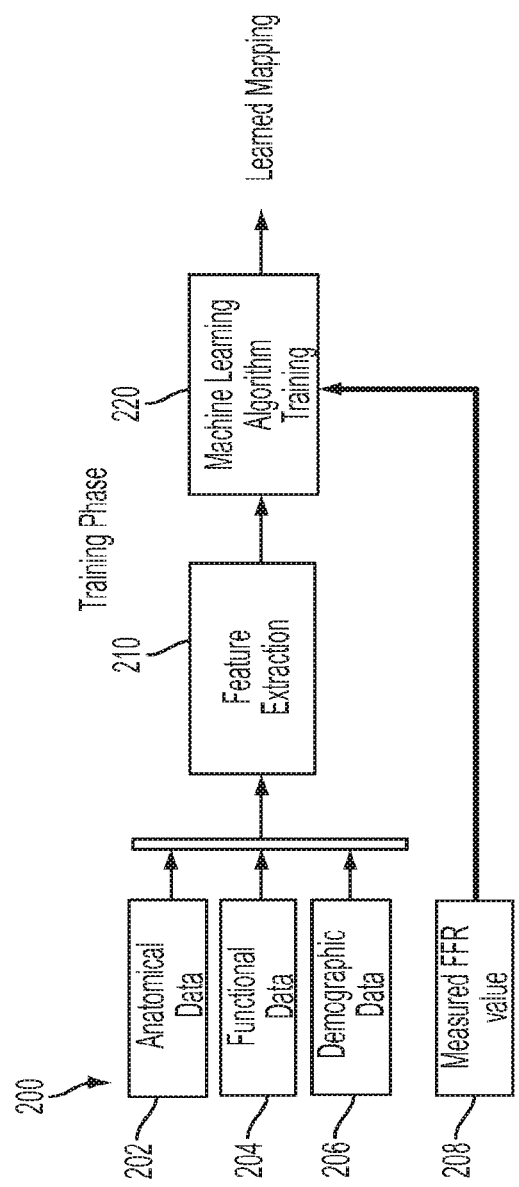
FIG. 2 illustrates a framework for implementing the method of FIG. 1 according to an embodiment of the present invention.

FIG. 1 illustrates a method of training a machine-learning based mapping for determining FFR according to an embodiment of the present invention. The method of FIG. 1 is used to implement the training phase that results in a trained mapping for determining FFR. FIG. 2 illustrates a framework for implementing the method of FIG. 1 according to an embodiment of the present invention.

Referring to FIG. 1, at step 100, training data is received. The training data is a database of stenoses from multiple patients, with each stenosis having a ground truth FFR value. The ground truth FFR value for each stenosis can be an invasively measured FFR value. FIG. 2 illustrates a framework for implementing the method of FIG. 1 according to an embodiment of the present invention. As shown in FIG. 2, the training data 200 can include anatomical data 202, functional data 204, and demographic data 206 for each training instance, as well as the ground truth measured FFR value 208 for each training instance. The anatomical data 202 can include one or more medical images of the stenosis. For example, the anatomical data 202 can include medical imaging data obtained using one or more medical imaging modalities, such as Computed Tomography (CT), X-ray angiography, Magnetic Resonance Imaging (MRI), Ultrasound, Intra-Vascular Ultrasound (IVUS), Optical Coherence Tomography (OCT), etc. The functional data 204 can include functional measurements, such as blood pressure, heart rate, and ECG measurements, as well as data relating to one or more medical imaging tests for a patient, such as data from a perfusion scan (e.g., SPECT, PET, etc.) or data related to contrast agent propagation in medical images. The demographic data 206 can include demographic information, such as age, gender, height, and weight, etc. Although not shown in FIG. 2, the training data can also include various other types of data, such as in-vitro diagnostics data, genotype of the patient, lifestyle factors of the patient, and patient history.

At step 110, features are extracted from the training data. This feature extraction step is shown as step 210 of FIG. 2. In particular, a set of features is extracted for each training instance (i.e., each measured FFR value). The set of features for each training instance can include anatomical, functional, diagnostics, molecular, and/or demographic measurements. The anatomical features may be extracted from the medical imaging data. The anatomical features can include anatomical measurements characterizing the stenosis, as well as other anatomical measurements for associated regions such as the heart, the coronary vessel tree, the myocardium, and the aorta. Depending on the source and type of the input data, the extracted features may be binary, numerical, categorical, ordinal, binomial, interval, text-based, or combinations thereof.

Figure 3:
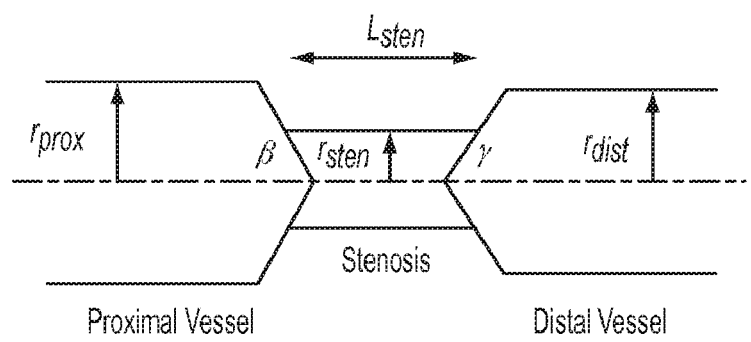
FIG. 3 illustrates geometric features characterizing the shape of a stenosis.

According to an advantageous implementation, the anatomical features extracted from medical image data can include parameters characterizing the geometry of the stenosis, such as reference diameters of the vessel proximal and distal to the stenosis, minimal lumen diameter (MLD) within the stenosis, lesion length (LL), entrance angle of the stenosis, entrance length, exit angle of the stenosis, exit length, percentage of the diameter blocked by the stenosis, and the percentage of the area blocked by the stenosis. It is also possible that additional parameters characterizing the geometry of the stenosis can be extracted, as well, or various parameters can be combined to generate additional features. According to an advantageous embodiment, the features characterizing the geometry of the stenosis can be automatically extracted using the method described in U.S. Pat. No. 8,526,699, which is incorporated herein by reference. FIG. 3 illustrates geometric features characterizing the shape of a stenosis. In particular, FIG. 3 shows the radius $r_{prox}$ of the proximal vessel, the radius $r_{dist}$ of the distal vessel, the lesion length $L_{sten}$ of the stenosis, the radius $r_{sten}$ of the stenosis, the entrance angle $\beta$ of the stenosis, and the exit angle $\gamma$ of the stenosis.

The anatomical features extracted from the medical image data can also include parameters characterizing the morphology of the stenosis, such as characteristics of calcification, characteristics of the plaque, characteristics of thrombus, characteristics of diffuse disease (i.e., single stenosis or diffused stenosis along artery), the presence of total or sub-total occlusion (i.e., complete blockage or partial blockage), and the presence of myocardial bridging. The parameters characterizing the morphology of the stenosis can be binary parameters indicating presence or absence or numerical values indicating a grading for a particular parameter.

The anatomical features extracted from the medical image data can also include parameters characterizing the geometry of the vessel branch bearing the stenosis, such as vessel radius and areas sampled along the centerline of the branch, terminal radius and area of the vessel branch, centerline tortuosity measures, the location of the stenosis in the branch (e.g., proximal, mid, or distal in the branch), a cumulative number of vessel narrowings in the branch proximal to the stenosis of interest, and a cumulative number of calcifications within the branch proximal to the stenosis of interest.

The anatomical features extracted from the medical image data can also include parameters characterizing the entire coronary artery tree, such as an indication of left or right dominance, size of coronary territories associated with myocardial masses, terminal radius of each coronary branch, number of lesions (stenoses) in the entire coronary tree, an indication of which segments of the coronary artery tree has lesions, bifurcations (type and angulations), trifurcations (type and angulations), the number and location of stents already implanted, and the number and location of bypass grafts. The "type" of each bifurcation and trifurcation refers to a characterization of each bifurcation and trifurcation as one of a set of predetermined types.

The anatomical features extracted from the medical image data can also include parameters characterizing cardiac anatomy and function, such as end-systolic volume (ESV), end-diastolic volume (EDV), ejection fraction (EF), endocardial volume, epicardial volume, myocardial volume, trabeculae and papillary muscle volume and mass, left and right ventricular volume and mass, characteristics of contrast agent attenuation (e.g., different intensity values for each voxel from different frames of a medical image sequence), and characteristics of contrast agent propagation (e.g., a number of frames to propagate contrast agent).

Additional features may be extracted from functional measurements and/or demographic information for a patient associated with each training instance. Such features can include systolic blood pressure, diastolic blood pressure, mean arterial pressure, heart rate at rest and/or during stress, parameters derived from an ECG trace (e.g., QRS duration, R-R interval, etc.), past history of heart disease, past history of valve dysfunction, past history of valve repair or replacement, body mass index (BMI), body surface area (BSA), weight, height, age, and sex. The features for the patient's past history may be binary, indicating that there is a past history or not, or categorical, providing further indication of a category of the past history.

In addition to the anatomic and morphological features extracted from medical images, functional features may also be extracted from one or more medical imaging tests for a patient. For example, data from a perfusion scan, such as SPECT, PET, etc., may be used to extract features such as metrics characterizing relative and/or absolute tissue perfusion in each coronary artery at rest and/or during stress. Another example is using angiographic data to extract characteristics of contrast agent propagation, which may be quantified by metrics such as time-to-peak, peak density, and time-averaged density from a time-density curve.

In addition to the above describe features, several derived features may also be computed from the extracted features. These derived features may be represented as linear or non-linear combinations of the extracted features. For example, lesion length (LL) and minimal lumen diameter (MLD) may be combined to obtain a new feature (LL/

MLD^4), which could then be used in the training database. Furthermore, molecular information as measured by in-vitro diagnostic tests (e.g., serum test indicating the level of myocardial damage, inflammation, etc.), and diagnostic information regarding the nature of blockage (e.g., fibrotic, calcified, etc.) primarily derived from imaging and other diagnostic test can be utilized to generate additional features.

The feature extraction from the medical image data for each training instance may be fully automated, semi-automated, manual, or a combination thereof. According to advantageous implementation, in a fully-automated feature extraction approach, one or more underlying image processing algorithms to first detect the anatomical region of interest and then extract the anatomical features. For example, the image-processing algorithms may automatically detect the stenosis, coronary vessels, coronary ostium, cardiac chambers, myocardium, trabeculae and papillary muscles, and aorta, and then extract all the required anatomical features from the medical image data in the detected regions. The automated feature selection can be performed using the methods described in U.S. Pat. No. 8,526,699, United States Published Patent Application No. 2013/0216110, U.S. Pat. No. 8,582,854, and U.S. Pat. No. 8,116,548, each of which is incorporated herein by reference. Under a semi-automated approach, some of the features may be extracted automatically, while some others may be annotated, edited, or corrected by a user. Under a manual approach, the features are annotated or measure by a user. The feature extraction step may be performed on a medical image scanner, or on another device, such as an imaging workstation.

Returning to FIG. 1, at step 120, a mapping between the ground truth FFR values and the extracted features is trained using a machine learning algorithm. Once the training database is assembled together with the ground-truth, the mapping between the input features and the ground truth FFR values is determined by using a machine learning algorithm. The type of machine learning algorithm used to train the mapping may be a supervised, semi-supervised, transductive, or reinforcement based learning algorithm. According to an advantageous embodiment, the trained mapping is a learned empirical model that combines the extracted features with various learned weights.

In an advantageous embodiment, we an image-based boosting ridge regression method is used to train the mapping. The complexity of the output manifold relating the functional parameters to the input measurements can be captured by extending the image-based boosting ridge regression (IBRR) method described in U.S. Pat. No. 7,949,173, which is incorporated herein by reference. The IBRR method is able to encapsulate the non-linear relationship between image features, image context information, and anatomical object parameters such as difference in position, orientation and scale relative to current image sample. In the present application, the input measurement space is extended to include parameters characterizing the geometry of the stenosis, morphology, geometry of the branches, geometry of the entire cardiac tree, cardiac anatomy and function, and/or other functional or demographic information, in addition to direct image-based features. The output space, in the present application, is a value for the hemodynamic index of interest (e.g., pressure-drop, FFR, CFR, iFR, BSR, HSR, IMR). The extended image-based boosting regression (EIBRR) minimizes a cost function which combines a regression output fidelity term (difference between predicted and ground truth output) and a regularization term. EIBRR uses an additive output function which aggregates a set of weak regression stumps combined with ridge regression (Tikhonov regularization) and an incremental feature selection scheme. Using the incremental feature selection scheme, EIBRR selects a subset of features from the available inputs that can predict the output while discarding features that are not relevant to the output manifold. EIBRR is able to efficiently model complex or non-linear manifolds.

In alternative embodiments, other machine learning algorithms may also be used to train the machine-learning based mapping for determining FFR or other hemodynamic indices. For example, machine learning algorithms, such as regression algorithms (linear, non-linear, or logistic), decision trees or graphs, association rule learning, artificial neural networks, support vector machines, inductive logic programming, Bayesian networks, instance-based learning, manifold learning, sub-space learning, deep learning, dictionary learning, etc., may be used to train the machine-learning based mapping.

EIBRR is described in greater detail below by first describing an extended image-based boosting regression (EIBR) training method, and then describing the EIBRR training method.

The following notation is used herein: a is a scalar, a is a column vector, and A is a matrix. The input is denoted by $x \in R^d$, the output by $y(x) \in R^q$, the regression function by $g(x): R^d \to R^q$ and the training data points by $\{(x_n, y_n); n=1, 2, \ldots, N\}$. Further, we denote $x^T A x = \|x\|_A^2$ and $tr\{X^T A X\} = \|X\|_A^2$.

EIBR minimizes the following cost function, which combines a regression output fidelity term and a subspace regularization term:

$$J(g) = \sum_{n=1:N} \{\|y(x_n) - g(x_n)\|_A^2 + \lambda \|\mu - g_t(x_n)\|_B^2\}, \quad (3)$$

where $\lambda$ is a regularization coefficient.

EIBR assumes that the regression output function $g(x)$ takes an additive form:

$$g_t(x) = g_{t-1}(x) + \alpha_t h_t(x) = \sum_{i=1:t} \alpha_i h_i(x), \quad (4)$$

where each $h_i(x): R^d \to R^q$ is a weak learner (or weak function) residing in a dictionary set $H$, and $g(x)$ is a strong learner (or strong function). Boosting is an iterative algorithm that leverages the additive nature of $g(x)$: At iteration t, one more weak function $\alpha_t t_t(x)$ is added to the target function $g_t(x)$. Accordingly, $$J(g_t) = \sum_{n=1:N} \{\|r_t(x_n) - \alpha_t h_t(x_n)\|_A^2 + \lambda \|s_t(x_n) - \alpha h_t(x_n)\|_B^2\}, \quad (5)$$

where $r_t(x) = y(x) - g_{t-1}(x)$ and $s_t(x) = \mu - g_{t-1}(x)$.

The optimal weak function $\hat{h}$ (dropping the subscript t for notational clarity) and its weight coefficient $\hat{\alpha}$, which maximally reduce the cost function (or boost the performance) are given as follows:

$$\hat{h} = \arg\max_{h \in \mathcal{H}} \epsilon(h), \; \hat{\alpha}(\hat{h}) = \frac{tr\{(AR + \lambda BS)\hat{H}^T\}}{\|\hat{H}\|_{A+\lambda B}^2}, \quad (6)$$

where

-continued $$\epsilon(h) = \frac{tr\{(AR + \lambda BS)H^T\}}{\sqrt{\|H\|^2_{A+\lambda B}}\sqrt{\|R\|^2_A + \lambda\|S\|^2_B}},\quad(7)$$

and the matrices $R_{q \times N}$, $S_{q \times N}$, and $H_{q \times N}$ are defined as: $R=[r(x_1), K, r(x_N)]$, $S=[s(x_1), K, s(x_N)]$, $H=[h(x_1), K, h(x_N)]$, respectively. Finally, EIBR invokes shrinkage (with the shrinkage factor $\eta=0.5$) leading to a smooth output function: $g_t(x)=g_{t-1}(x)+\eta\alpha_t h_t(x)$.

The entire input feature set is used to construct one-dimensional (1D) decision stumps as primitives of the dictionary set H. A 1D decision stump h(x) is associated with a feature index f, a feature value v(x; f), a decision threshold $\epsilon$, and a binary direction indicator p, i.e., $p \in \{-1,+1\}$. Such a 1D decision stump can be expressed as:

$$h(x; \mu) = \begin{cases} +1 & \text{if } pf(x;\mu) \geq p\epsilon \\ -1 & \text{otherwise} \end{cases}.\quad(8)$$

For image-based features, given a moderate image size, a large number of image features can be generated by varying their attributes. The number of features can be denoted by M. By adjusting the threshold $\epsilon$, e.g., K evenly spaced levels, K decision stumps can be created per feature, such that 2KM 1D decision stumps are created.

A weak function is constructed as a q-dimensional (q-D) decision stump $h(x)_{q \times 1}$ that stacks q 1D decision stumps. This can be expressed as:

$$h(x; f_1, \ldots, f_q)=[h_1(x; f_1), \ldots, h_q(x; f_q)]^T.\quad(9)$$

Because each $h_j(x; f_j)$ is associated with a different feature, it is possible to construct a sufficiently large weak function set that contains $(2KM)^q$ weak functions.

Boosting operates as a feature selector, such that at each round of boosting, the features that maximally decrease the cost function in Equation (5) are selected. However, to transform the boosting algorithm into an efficient implementation, there is computational bottleneck that is the maximization task in Equation (6). This maximization task necessitates a greedy feature selection scheme, which can be too expensive to evaluate because it involves evaluating $(2MNK)^q$ decision stumps for each boosting round.

EIBR utilizes an incremental feature selection scheme by breaking q-D regression problem into q dependent 1D regression problems. Using the incremental vector:

$$h^i(x)_{i \times 1} \times [h_1(x), \ldots, h_i(x)]^T=[h^{i-1}(x)^T \cdot h_i(x)]^T,\quad(10)$$

the optimal $h_i(x)$ is searched to maximize the $\epsilon(h^i)$, which is similarly defined in (7) but based on all i ($i \leq q$) dimensions processed so far. The incremental selection scheme needs to evaluate only 2qMNK decision stumps with some overhead computation while maintaining the dependence among the output dimension to some extent.

The EIBR described above has two drawbacks. First, it is restrictive to use the subspace regularization term $\|\mu - g(x_n)\|_B^2$ in (3), which amounts to a multivariate Gaussian assumption about the output variable that often manifests a non-Gaussian structure for real data. As a result, the generalization capability is hampered. Second, the weak function h(x) can be too "weak" as it consists of several 1D binary decision stumps $h_j(x)$ sharing the same weight coefficient $\alpha$. Consequently, the training procedure can take a long time, and the trained regression function uses too many weak functions, which can affect the running speed. EIBRR, which is described in detail below, overcomes the drawbacks of EIBR by replacing the subspace regularization and enhancing the modeling strength of the weak function.

Instead of using the 1D decision stumps as primitives, the EIBRR method uses regression stumps. A regression stump h(x; f) is defined as:

$$h(x; f) = \sum_{k=1:K} w_k [v(x; f) \in R_k] = e(x; f)^T w,\quad(11)$$

where [.] is an indicator function, v(x; f) is the feature value with index f, and $\{R_k; k=1,2,K, K\}$ are evenly spaced intervals. In Equation (11), all the weights $w_k$ are compactly encoded by a weight vector $w_{K \times 1}=[w_1, w_2, K, w_K]^T$ and the vector e(x; f) is some column of the identity matrix: only one element is one and all others are zero. Similarly, the weak function $h(x)_{q \times 1}$ is constructed by stacking q different 1D regression stumps, i.e., $$h(x; f_1, \ldots, f_q)=[e_1(x; f_1)^T w_1, \ldots, e_q(x; f_q)^T w_q]^T,\quad(12)$$

where $w_j$ is the weight vector for the $j^{th}$ regression stump $h_j(x; f_j)$. The weights belonging to all regression stumps can be further encoded into a weight matrix $w_{K \times q}=[w_1, w_2, K, w_q]$. Since we now use the weights, we drop the common coefficient $\alpha$ in the regression output function defined in Equation (4), and instead express the regression function as follows:

$$g_t(x) = g_{t-1}(x) + h_t(x) = \sum_{i=1:t} h_i(x).\quad(13)$$

It is easy to verify that a regression stump can be formed by combining multiple decision stumps. Such a combination strengthens the modeling power of weak functions and consequently accelerates the training process. Empirical evidence shows that the training time is almost inversely proportional to the number of levels used in the weak function. Although using the regression stump brings the risk of overfitting, this risk can be ameliorated by considering the model complexity of the regression stump.

Ridge regression, also known as Tikhonov regularization, is a method of regularization for an ill-conditioned system of linear equations. Ridge regression principles are adopted into a boosting framework in order to train a regression function using EIBRR. The model complexity of the regression output function $g_t(x)$ depends on its weight matrices $\{W_1, W_2, K, W_t\}$. Because boosting regression proceeds iteratively, at the $t^{th}$ boosting iteration, the following ridge regression task is performed that only involves the weight matrix $W_t$ (dropping the subscript t for notational clarity):

$$\arg\min_W \left\{ J(g) = \sum_{n=1:N} \{\|r(x_n) - h(x_n)\|_A^2 + \lambda\|W\|_B^2\} \right\}.\quad(14)$$

Because the weight vectors $\{w_1, w_2, K, w_q\}$ in the weight matrix W are associated with q different local rectangle features, the optimization in (14) implies two subtasks:

1. Given a set of q features with selector indices $f_1, K, f_q$, respectively, find the optimal matrix $\hat{W}(f_1, K, f_q)$ and the minimum cost $\hat{J}(f_1, K, f_q)$; and 2. Find the optimal set of q features with respective selector indices attributes $\hat{f}_1, K, \hat{f}_q$ that minimizes the minimum cost $\hat{J}(f_1, K, f_q)$. This corresponds to feature selection.

The optimization in (14) necessitates a greedy feature selection that may be computationally unmanageable. Accordingly, it may be advantageous to resort to a suboptimal, yet computationally amenable, incremental feature selection method. Accordingly, we introduce the following "incremental" vectors and matrices:

$$A^i = \begin{bmatrix} A^{i-1} & a^{i-1} \\ a^{i-1T} & a_i \end{bmatrix}, h^i = \begin{bmatrix} h^{i-1} \\ h_i \end{bmatrix}, r^i = \begin{bmatrix} r^{i-1} \\ r_i \end{bmatrix}.$$

Assuming that features have been selected up to i−1, that is the incremental vector $h^{i-1}(x; f_1, K, f_{i-1})$ and the weight vectors $w_1, K, w_{i-1}$ are known, the IBRR method aims to find the weak function $h^{i-1}(x; f_i) = e_i(x; f_i)^T w_i$ that minimizes the following ridge regression cost $J^i(f_i, w_i)$ (referred to herein as the EIBRR cost function):

$$J^i(f_i, w_i) = \sum_{n=1:N} \{\|r^i(x_n) - h^i(x_n)\|_{A^i}^2 + \lambda \|w_i\|_B^2\}. \quad (15)$$

It can be derived that, for a fixed $f_i$, the optimal weight vector is:

$$\hat{w}_i(f_i) = \Gamma_i(f_i)^{-1} \tau_i e_i(x; f_i), \quad (16)$$

where $$\Gamma_i(f_i) = \lambda B + \sum_{n=1:N} \{e_i(x_n; f_i) a_i e_i(x_n; f_i)^T\}, \quad (17)$$

$$\tau_i = \sum_{n=1:N} \{(r^{i-1}(x_n) - h^{i-1}(x_n))^T a^{i-1} + r_i(x_n)^T a_i\}. \quad (18)$$

Accordingly, the EIBRR method searches for the optimal $f_i$ to minimize the IBRR cost function $J^i(f_i, \hat{w}_i(f_i))$.

When $A=B=I_q$, the incremental feature selection gives the optimal solution. In this case, the optimal weight $w_{j,k}$ for the $j^{th}$ weak function is the weighted average:

$$w_{j,k} = \frac{\sum_{n=1}^{N} r_j(x_n)[f(x_n; f_j) \in R_k]}{\lambda + \sum_{n=1}^{N} [f(x_n; f_j) \in R_k]}. \quad (19)$$

The order of the dimension of the output variable can be randomly permutated in order to improve robustness and remove bias. It is also possible to improve efficiency by randomly sampling the dictionary set, i.e., replacing M with a smaller M', and randomly sampling the training data set, i.e., replacing N with a smaller N'.

FIG. 4 illustrates an algorithm for training a machine-learning based mapping using EIBRR according to an embodiment of the present invention. At 402, the IBRR tuning parameters are initialized. In particular, the normalization matrices A and B, the regularization coefficient λ, and the shrinkage factor η are set. These may be set automatically or manually by a user. Stopping criteria, such as a maximum number of iterations $T_{max}$ and a minimum cost function value $J_{min}$ are also set. Initial values for t=0, $g_0(x)=0$, and $r_0(x)=y(x)$ are also set.

At 404, an optimal weak function is determined based on a set of image features. The optimal weak function is determined to minimize the EIBRR cost function (15). Step 404 is described in greater detail in FIG. 5.

At 406, the regression function is updated based on the optimal weak function determined in 404. As shown in (13) the regression function is updated at each iteration by adding the optimal weak function for that iteration to the prior regression function, such that the final regression function is the sum of the weak functions for all of the iterations. Accordingly, when the weak function is determined, it is added to the prior regression function.

At 408, the approximation error and EIBRR cost function are evaluated based on the updated regression function. The approximation error tests the regression function by comparing difference vector based on input training data resulting from the regression function to the known output training data. The EIBRR cost function is expressed in (15).

At step 410, it is determined whether the IBRR method has converged. In order for the method to converge, it is determined whether a stop condition is met. For example, convergence can be achieved if the cost function is less than the minimum cost function $J_{min}$. It is also possible that convergence is achieved when the maximum number of iterations $T_{max}$ has occurred, when the approximation error $r_t(x)$ is less than a certain threshold, when the difference between the cost function at the previous step and the current step is less than a certain threshold, or when the difference between the approximation error at the previous step and the current step is less than a certain threshold. If the EIBRR algorithm has not converged at 410, the algorithm returns to step 404 and repeats steps 404, 406, and 408 until convergence is achieved. If the EIBRR algorithm has converged at step 510, the trained regression function is stored or output. The trained regression function resulting from the method can be stored in a memory or storage of a computer system or output for use in determining hemodynamic indices, such as FFR, in new patient datasets.

FIG. 5 illustrates a feature selection algorithm according to an embodiment of the present invention. This method corresponds to step 404 of FIG. 4. At 502, the dimension of the weak function is set. As described above, the dimension of the weak function can be permutated in order to improve robustness and remove bias. The dimension of the weak function determines how many image features are used to determine each weak function.

At 504, an image feature is selected to minimize the EIBRR cost function (15). The image feature is selected by looping over each of the image features in the feature dictionary set M to find the feature that most minimizes the IBR cost function (15). As shown at 503 of FIG. 5, it is possible that a reduced dictionary set M' be sampled from the dictionary set M and used in place of M for feature selection in order to improve computational efficiency. Also, as shown at 503 of FIG. 5, a reduced set N' of training data may be sampled from the training set N in order to improve computational efficiency.

At step 506, the weak function is updated. As described above, the weak function is constructed by stacking q different 1D regression stumps. Each of the regression stumps uses an image feature. Once an image feature is selected at step 504, the weak function augments the current feature to previously selected features in an incremental fashion. As shown in FIG. 5, steps 504 and 506 are iterated over the dimension q. That is the algorithm repeats steps 504 and 506 until q image features have been selected for the weak function. Once q image features have been selected, the weak function is output or stored. The weak function resulting from the combination of the selected features can be output for continued use in the EIBRR method of FIG. 4. The weak function may be stored in memory or storage of a computer system. The weak functions stored in each iteration of the EIBRR method of FIG. 5 can be combined to generate the trained regression function.

Figure 6:
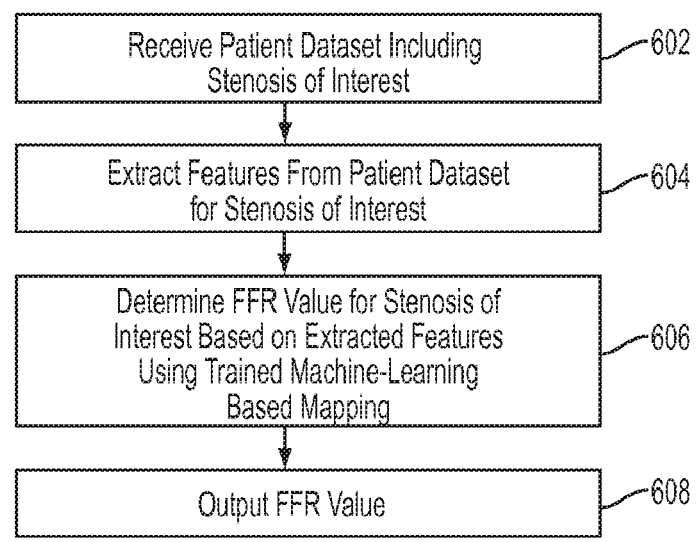
FIG. 6 illustrates a method for determining FFR for a patient using a trained machine-learning based mapping according to an embodiment of the present invention.

Once the machine-learning based mapping is trained, the trained mapping is stored in a memory or storage of a computer system and is then used to determine an FFR value (or other hemodynamic index value) for new patients. FIG. 6 illustrates a method for determining FFR for a patient using a trained machine-learning based mapping according to an embodiment of the present invention.

At step 602, a patient dataset including a stenosis of interest is received. The patient dataset includes medical image data of a patient. The medical image data can include medical images from any medical imaging modality, such as Computed Tomography (CT), X-ray angiography, Magnetic Resonance Imaging (MRI), Ultrasound, Intra-Vascular Ultrasound (IVUS), Optical Coherence Tomography (OCT), etc. The medical image data can be received by obtaining the medical image data using an image acquisition device, receiving the medical image data directly from an image acquisition device, or loading stored medical image data for the patient. The patient dataset can also include functional data, such as functional measurements (e.g., blood pressure, heart rate, ECG, etc.), and demographic data, as well as any other types of data from which features can be extracted. In some cases, the patient dataset may include multiple stenoses of interest.

At step 604, features are extracted from the patient dataset for the stenosis of interest. When there are multiple stenoses of interest, a respective set of features is extracted for each stenosis of interest. In particular, the same feature are extracted for the stenosis of interest as those extracted for each training instance in the training data. These features are described above with respect to step 110 of FIG. 1. According to advantageous implementation, a fully-automated feature extraction approach can be used to extract the features. For example, one or more underlying image processing algorithms can be used to first detect each anatomical region of interest and then extract the anatomical features. For example, the image-processing algorithms may automatically detect the stenosis, coronary vessels, coronary ostium, cardiac chambers, myocardium, trabeculae and papillary muscles, and aorta, and then extract all the required anatomical features from the medical image data in the detected regions. In one embodiment, coronary stenoses of interest are first automatically detected in the medical image data, and then a respective feature set is automatically detected for each stenosis of interest. The automated feature extraction can be performed using the methods described in U.S. Pat. No. 8,526,699, United States Published Patent Application No. 2013/0216110, U.S. Pat. No. 8,585,854, and U.S. Pat. No. 8,116,548, each of which is incorporated herein by reference. According to other possible implementations, some of the features may be extracted semi-automatically or manually by a user. The feature extraction step may be performed on a medical image scanner, or on another device, such as an imaging workstation.

At step 606, an FFR value is determined for the stenosis of interest based on the extracted features using a trained machine-learning based mapping. In particular, the machine-learning based mapping trained based on the training data using the method of FIG. 1 is used to calculate the FFR value for the stenosis of the patient based on the extracted features. According to an advantageous embodiment, the trained mapping is a learned empirical model that combines the extracted features with various learned weights. As described above, the trained machine-learning based mapping may be a regression function trained using image-based boosting ridge regression, for example using the extended image-based boosting ridge regression (EIBRR) method illustrated in FIGS. 4 and 5. If there is multiple stenoses of interest in the patient dataset, a respective FFR value is determined for each stenosis of interest using the respective set of features extracted for each stenosis of interest. In a possible implementation, the trained mapping can calculate the FFR value together with a confidence interval.

At step 608, the FFR value is output. For example, the FFR value can be displayed on a display device of a computer system. The FFR value can also be stored on a memory or storage of a computer system.

In a possible embodiment, a user can utilize the method of FIG. 6 to analyze the effect of different treatment scenarios, by appropriately changing the value of some features to reflect the post-treatment scenario. In this case, once the FFR value is output at step 608, a user input changing one or more features to reflect a treatment scenario is received from the user, and the FFR value is re-calculated based on the modified features using the trained machine-learning based mapping.

Figure 7:
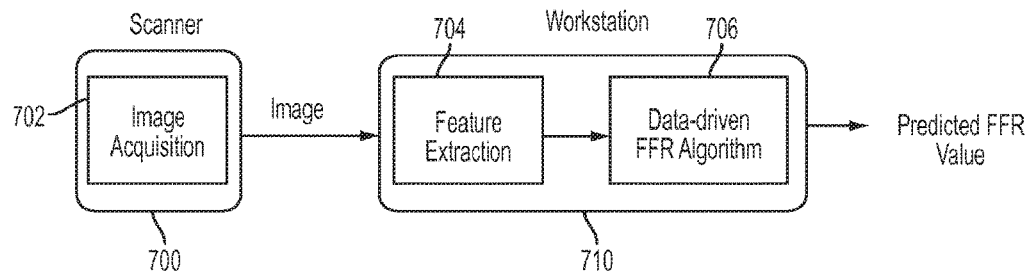
FIGS. 7, 8, and 9 illustrated various scenarios for implementing the method of FIG. 6.
Figure 8:
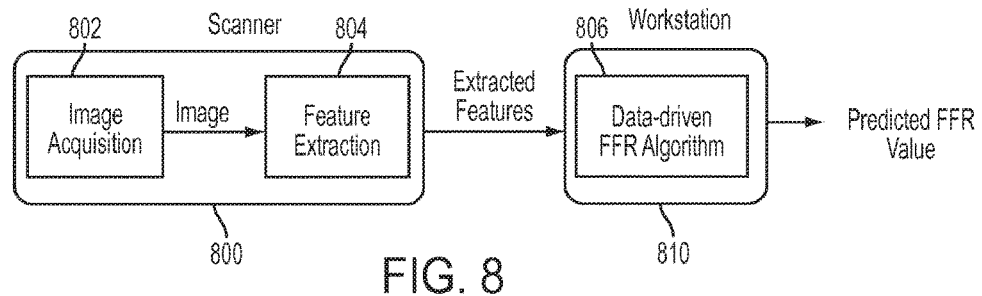
Figure 9:
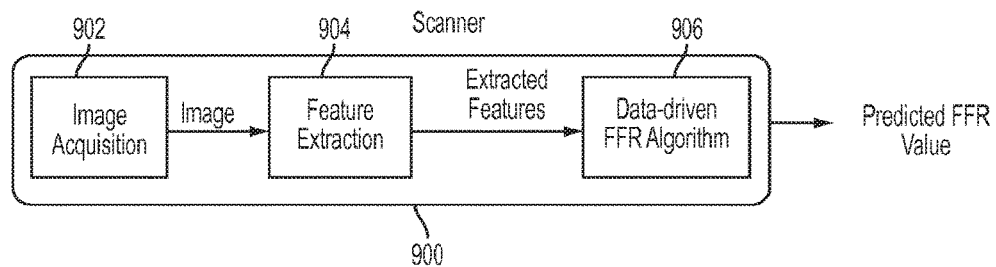

FIGS. 7, 8, and 9 illustrated various scenarios for implementing the method of FIG. 6. As shown in FIG. 7, in on embodiment, a scanner 700 (image acquisition device) is used for image acquisition 702, and the images are transferred from the scanner 700 to a workstation 710. The workstation 710 then performs the feature extraction 704 and FFR calculation 706 steps, resulting in the predicted FFR value. As shown in FIG. 8, in another embodiment, a scanner 800 performs the image acquisition 802 and feature extraction 804 and only the extracted image features are transferred from the scanner 800 to the workstation 810. The workstation then performs the subsequent FFR calculation 806, resulting in the predicted FFR value. As shown in FIG. 9, in another embodiment the scanner 900 performs the image acquisition 902, feature extraction 904, and the FFR calculation 906, resulting in the predicted FFR value.

As more data is collected, the training database containing the anatomical, physiological, and demographic measurements and/or features together with the ground truth invasive FFR measurements may grow in size. The updated database may then be used to re-train the machine-learning based mapping periodically. The new instances in the training database may be from unseen cases (i.e., cases that have not been used for either training or prediction in the past) or from cases which were used for prediction in the past, but now have invasive FFR measurements available. The training database may be either a central database of a local database for a particular institution. In a possible embodiment, instead of invasively hemodynamic quantities (such as FFR), the ground-truth values in the training database can be substituted by computational surrogates. For example, the ground truth FFR values for the training data may be replaced or complemented by an FFR value numerically computed using a mechanistic modeling approach.

According to a possible embodiment, instead of using patient-specific geometries during the training phase to compute the computational surrogates for FFR, synthetically generate geometries that are not based on patient-specific data can be used. Such geometries may be generated by varying the shape, severity, location, and number of stenoses, together with the radius and locations of main and side branches in a generic model of a coronary artery vessel tree. As a simplest example of a synthetically generated geometry, one can use a straight tube with a narrowing to represent the stenosis. Multiple CFD simulations can be performed by varying the synthetic geometry (e.g., minimum radius of the stenosis, entrance angle, exit angle) and varying the inflow or outflow boundary conditions to compute the FFR value. One advantage of using synthetically generated geometries is that it does not require the collection and processing of patient-specific data for completing the training phase, thereby saving both time and cost. Further, there is no limit on the type of synthetic geometries that can be generated, thereby covering a wide spectrum of vessel shapes and topology. Using this approach, the entire training phase can be performed without any patient-specific geometry or image data. United States Published Patent Application No. 2014/0024932, which is incorporated herein by reference, describes examples of CFD simulations on synthetically generated stenosis shapes.

As described above, various features can be extracted and used to train a machine-learning based mapping and to determine the FFR value. It is to be understood that the method described above is adaptive to patient features that are available and more or less features can be used. The methodology described above can be similarly used for other applications as well, such as determining the severity of other vascular stenosis, such as renal artery stenosis, aortic stenosis, peripheral artery stenosis, etc., determining the rupture risk for aneurysms, such as cerebral aneurysms, abdominal aortic aneurysms, etc., and classifying heart failure patients as a likely responder or non-responder to Cardiac Resynchronization Therapy (CRT).

According to another embodiment of the present invention, instead of extracting features from the medical image data, a machine learning algorithm is applied directly on the image voxels (or sets of voxels or volume patches) to learn the association between those voxels and the hemodynamic quantity of interest (e.g., FFR). In this embodiment, the problem of calculating FFR (or other hemodynamic quantities of interest can be solved in two phases. In the first phase, anatomically significant image patches are localized in an input 3D medical image. The image patches of interest can be localized using Marginal Space Deep Learning (MSDL) or Marginal Space Deep Regression (MSDR), which are machine learning methods that train a series of deep neural networks to detect the image patches of interest in a series of marginal parameter spaces with increasing dimensionality. In the second phase, for each image patch containing a stenosis along with other overlapping patches containing the rest of the coronary anatomy, a regressor trained using a deep neural network is used to computer an FFR value specific to that stenosis. The process is then repeated for each stenosis within the coronary tree as necessary.

Figure 10:
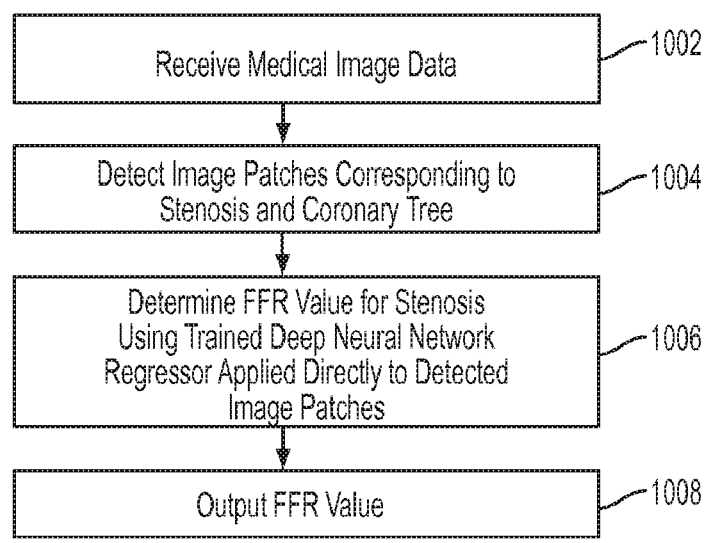
FIG. 10 illustrates a method for determining FFR using trained deep neural networks applied directly to medical image data of the patient.

FIG. 10 illustrates a method for determining FFR using trained deep neural networks applied directly to medical image data of the patient. Referring to FIG. 10, at step 1002, medical image data of the patient is received. In an advantageous implementation, the medical image data is a 3D medical image, but the present invention is not limited thereto. The medical image data can include medical images from any medical imaging modality, such as Computed Tomography (CT), X-ray angiography, Magnetic Resonance Imaging (MRI), Ultrasound, Intra-Vascular Ultrasound (IVUS), Optical Coherence Tomography (OCT), etc. The medical image data can be received by obtaining the medical image data using an image acquisition device, receiving the medical image data directly from an image acquisition device, or loading stored medical image data for the patient.

At step 1004, image patches corresponding to the stenosis and the coronary tree of the patient are detected in the medical image data. According to an advantageous implementation, a set of image patches are localized to signify all stenotic regions (image patches of a certain size surrounding each stenosis), coronary ostia (image patches centered around each ostium), coronary vessels (image patches around tubular coronary structures), and coronary bifurcation and trifurcations.

According to an advantageous embodiment, the image patches of interest can be detected using Marginal Space Deep Learning (MSDL) or Marginal Space Deep Regression (MSDR) applied directly to the voxels of the 3D medical image, which are machine learning methods that train a series of deep neural networks to detect the image patches of interest in a series of marginal parameter spaces with increasing dimensionality. MSDL and MSDR utilize deep learning to automatically learn high-level domain-specific image features directly from the medical image data.

In both MSDL and MSDR, in order to detect an object, the parameter space of the target object is divided into a series of marginal search spaces with increasing dimensionality and a respective deep multi-layer neural network is trained for each marginal search space. In MSDL, each trained deep neural networks is discriminative, in that it calculates, for a given hypothesis in the search space, a probability that the hypothesis in the search space is correct. In MSDR, each trained deep neural network provides a regression function (regressor) that calculates, for each hypothesis in the search space, a difference vector from that hypothesis to predicted pose parameters of the object in the search space.

Figure 11:
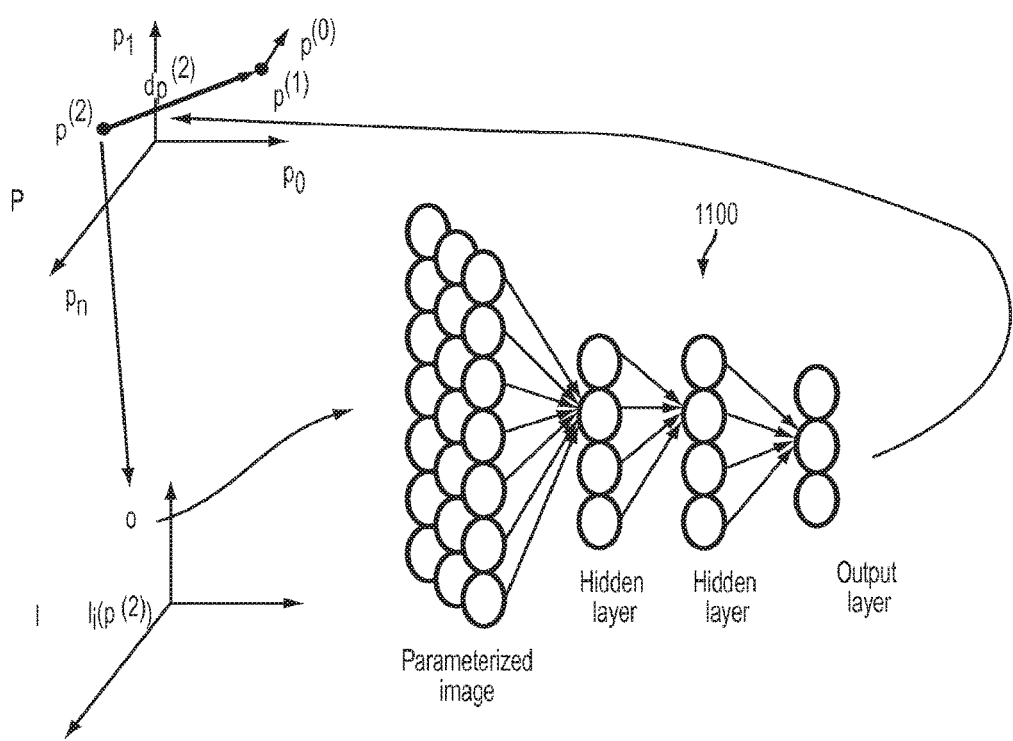
FIG. 11 illustrates training a deep multi-layer neural network regressor for a particular parameter space.

The deep neural networks are trained using a database of training images. In order to train the deep neural networks, given a database of training images with the target object annotated in all or a subset of the training images, the object location (pose) is parameterized and the marginal spaces hierarchy is established. For example a set of parameters for the object location can be the rigid translation (position) (x, y, z), rotation (orientation) ($\theta_x$, $\theta_y$, $\theta_z$), and scale ($s_x$, $s_y$, $s_z$), and the marginal spaces can be translation, translation+rotation, and translation+rotation+scale. The range of the parameterized spaces is determined from the annotated training image subset. Next, hypotheses are generated in the current search space. For the first search space, the hypotheses are generated directly from the current range, and for the other search spaces, the hypotheses are generated from the current hypotheses set augments with additional parameters which are sampled from the current corresponding range. Given the set of hypotheses for the current search space, a deep multi-layer neural network is trained having as input the sub-image parameterized by the corresponding hypothesis parameters and as output the difference between the current parameters and the target or ground truth parameters for the current search space. FIG. 11 illustrates training a deep multi-layer neural network regressor for a particular parameter space. As shown in FIG. 11, P is the current parameter space (marginal space), $p^{(2)}$ is the parameters of a hypothesis in the parameter space, from which an image is generate from the $i^{th}$ image $I_i(p^{(2)})$ in the image space I. The parameterized image is used as input to a multi-layer deep neural network 1100 and the supervised output is given by the parameter difference $dp^{(2)}$ between the hypothesis parameters $p^{(2)}$ and the ground truth parameters $p^{(1)}$ in the current parameter space P and optionally a confidence measure. The deep neural network 1100 can be trained directly on the difference to the ground truth (in which case $p^{(1)}$ is the annotated parameter set) or the deep neural network 1100 can be trained on a displacement towards ground truth.

For the deep neural network architecture and training, various types of neural networks can be used, such as convolutional neural networks (CNN), stacked restricted Boltzmann machine (RBM), or stacked auto-encoders (AE). In the case of RBM or AE, we can pre-train the networks in an unsupervised manner using all of the available images (not annotated) to determine the representative features that characterize the class of data from a large database, prior to supervised training using the subset of annotated training images. In an advantageous embodiment, the deep neural network is trained using a stacked denoising auto-encoder (DAE) in two stages. The first stage is unsupervised where each layer of the multi-layer deep neural network is trained to reconstruct the input. In this stage, a virtual layer similar to the input is added to the output and the error to the input is minimized in this virtual layer. The second stage is supervised and the whole network error is minimized relative to the output training data starting from the pre-trained network weights. One characteristic of the DAE is that it randomly drops a certain percentage (up to 50%) of the inputs during training, which significantly increases the robustness of the resulting regressor. The output parameter space can be either directly regressed using a linear function or it can be discretized relative to the parameter range as solved as a multi-class classification problem. The second formulation has an advantage that it can directly encode the output probability and can generate multiple hypotheses.

The set of current hypotheses are then propagated through the trained deep neural network, and in a possible embodiment, the new set of hypotheses can be iteratively refined using the same deep neural network or through a newly trained deep neural network. This iterative process can eliminate samples far from the solution (non-overlapping) and generate samples closer to the true position to improve precision. The new set of hypotheses is augmented with new parameters from the subsequent marginal space and the process is repeated for the subsequent marginal space. This results in a respective trained deep neural network (regressor or discriminative deep neural network) for each of the marginal spaces.

Figure 12:
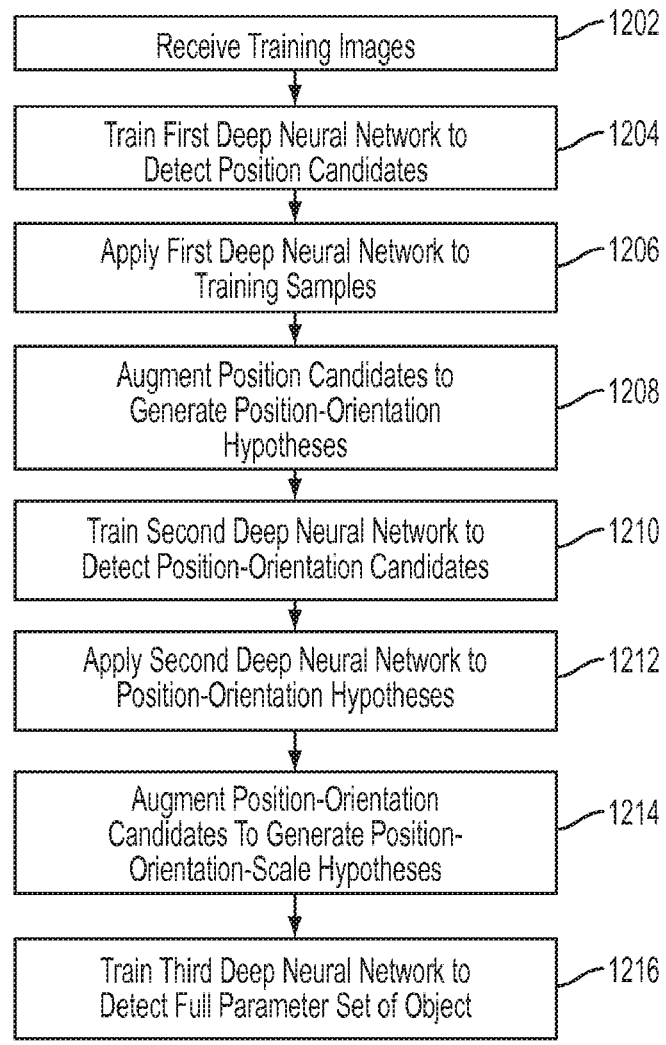
FIG. 12 illustrates a method of training series of deep neural networks for object detection according to an embodiment of the present invention.

FIG. 12 illustrates a method of training series of deep neural networks for object detection according to an embodiment of the present invention. The method of FIG. 12 can be used to train deep neural networks for detecting the image patches corresponding to the stenosis and coronary tree anatomy. Referring to FIG. 12, at step 1202, training images are received. In particular, a plurality of training images are loaded from a database. At least a subset of the training images are annotated with the pose (position, orientation, and scale) of the object of interest. The training images may also include non-annotated images as well.

At step 1204, a first deep neural network is trained to detect position candidates. In a possible implementation, the first deep neural network may be a discriminative deep neural network that inputs voxels of an image as hypotheses and for each voxel calculates a probability that an image patch centered at the voxel is the object of interest. In another possible implementation, the first deep neural network may train a regressive function that inputs voxels of an image as hypotheses calculates a difference vector for each input resulting in a predicted position calculated for each input voxel. At step 1206, training samples are passed through the trained first deep neural network and a number of best position candidates are kept.

At step 1208, the position candidates are augmented with orientation parameters to generate hypotheses in the position-orientation search space. For example, a plurality of position-orientation hypotheses can be generated for each position candidate by rotating each image patch centered at a position candidate to a plurality of possible rotations. The range of these rotations can be determined by the range of orientations of the ground truth objects in the annotated training data.

At step 1210, a second deep neural network is trained to detect position-orientation candidates. In a possible implementation, the second deep neural network may be a discriminative deep neural network that inputs image patches of an image corresponding to the hypotheses in the position-orientation search space and for each image patch calculates a probability that the image patch is the object of interest. In another possible implementation, the second deep neural network may train a regressive function that inputs image patches of an image corresponding to the hypotheses in the position-orientation search space and calculates a difference vector in the position-orientation parameter space for each input resulting in a predicted position and orientation and a corresponding image patch in the image. At step 1212, the position-orientation hypotheses are passed through the trained second deep neural network and a number of best position-orientation candidates are kept.

At step 1214, the position-orientation candidates are augmented with scale parameters to generate hypotheses in the position-orientation-scale search space. For example, a plurality of position-orientation-scale hypotheses can be generated for each position-orientation candidate by scaling each image patch corresponding to a position-orientation candidate to a plurality of possible scales. The range of these scales can be determined by the range of scales of the ground truth objects in the annotated training data.

At step 1216, a third deep neural network is trained to detect a full parameter set (position-orientation-scale) of the object of interest. In a possible implementation, the third deep neural network may be a discriminative deep neural network that inputs image patches of an image corresponding to the hypotheses in the position-orientation-scale search space and for each image patch calculates a probability that the image patch is the object of interest. In another possible implementation, the third deep neural network may train a regressive function that inputs image patches of an image corresponding to the hypotheses in the position-orientation-scale search space and calculates a difference vector in the position-orientation-scale parameter space for each input resulting in a predicted position, orientation, and scale and a corresponding image patch in the image.

In step 1004 of FIG. 10, when an input medical image of a patient is received, the trained deep neural networks are used to detect the image patches corresponding to the stenosis and coronary tree anatomy. The process for detecting the target object parameters is similar to the training process. The set of generated hypotheses is propagated through the trained deep neural networks and iteratively refined through the marginal spaces, resulting in position, orientation, and scale parameters defining each target image patch.

Returning to FIG. 10, at step 1006, an FFR value is determined for the stenosis by applying a trained deep neural network regressor directly to the detected image patches. The machine learning algorithm in this case is directly applied on the detected image patches, which contain the original structure of the medical image along with the associated label from step 1004. In training the deep neural network regressor used in step 1006, the goal is to learn the association between those image patches and the hemodynamic quantity of interest for specific stenosis (e.g., FFR or pressure drop). Using such an approach, it is not necessary to first extract anatomical features (such as radius of the stenosis, length of the stenosis, etc.) from the images.

Figure 13:
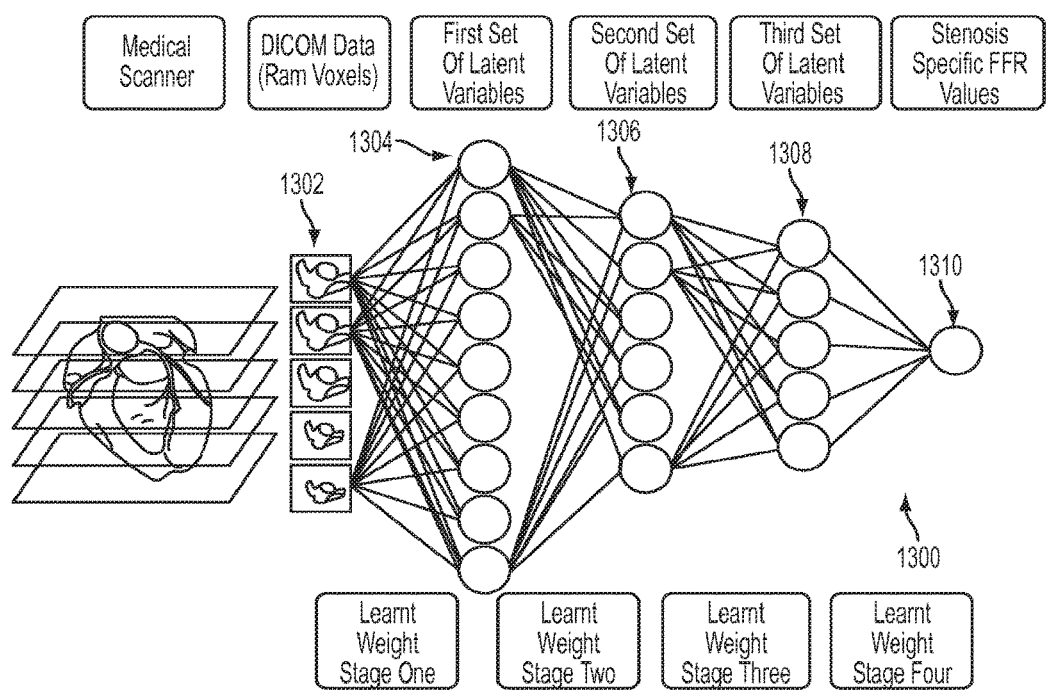
FIG. 13 illustrates applying a trained deep neural network regressor to image patches to determine an FFR value for a stenosis according to an embodiment of the present invention.

FIG. 13 illustrates applying a trained deep neural network regressor to image patches to determine an FFR value for a stenosis according to an embodiment of the present invention. As shown in FIG. 13, a deep neural network 1300 inputs the DICOM data (raw voxels) from the detected image patches 1302. The deep neural network is a multi-layer neural network with three layers 1304, 1306, and 1308 of latent variables, and a fourth layer 1310 that outputs a stenosis specific FFR value. Weights are learned to map the input voxels 1302 to the first set of latent variables 1304, the first set of latent variables 1304 to the second set of latent variables 1306, the second set of latent variables 1306 to the third set of latent variables 1308 and the third set of latent variables 1308 to the stenosis specific FFR value 1310. It is to be understood that the present invention is not limited to the specific number of layers shown in FIG. 13.

According to an advantageous embodiment, the deep neural network regressor for determining the FFR value of a stenosis can be trained as follows: (1) Collect a large set of trained image patches from medical images (e.g., Cardiac CT images) of various patients (e.g., 500+), but no matching FFR values (Dataset A). (2) Collect a large set of trained image patches from medical images (e.g., Cardiac CT images) of various patients (e.g., 200+) with identified stenosis image patches and corresponding FFR values. (Dataset B). (3) Set up the network by selecting the number of layers, the number of units per layer, the learning rate, and the initial random weights. These settings of the deep neural network can be determined experimentally. (4) Use Dataset A to train (i.e., tune) the weights of the deep neural network layer by layer using restricted Boltzmann machines (RBM) contrastive divergences, or Auto-encoders algorithms. No training is performed on the last layer in this step. (5) Use Dataset B to refine the weights of all layers (including the last layer) using a gradient descent back-propagation algorithm. During this step, L1 or L2 regularization can be used on the weights to avoid over-fitting.

In step 1006 of FIG. 10, once the image patches are detected in step 1004, the trained deep neural network regressor is applied directly to the detected image patches, which results in a stenosis specific FFR value for each stenosis.

Returning to FIG. 10, at step 1008, the FFR value is output. For example, the FFR value can be displayed on a display device of a computer system. The FFR value can also be stored on a memory or storage of a computer system.

Figure 14:
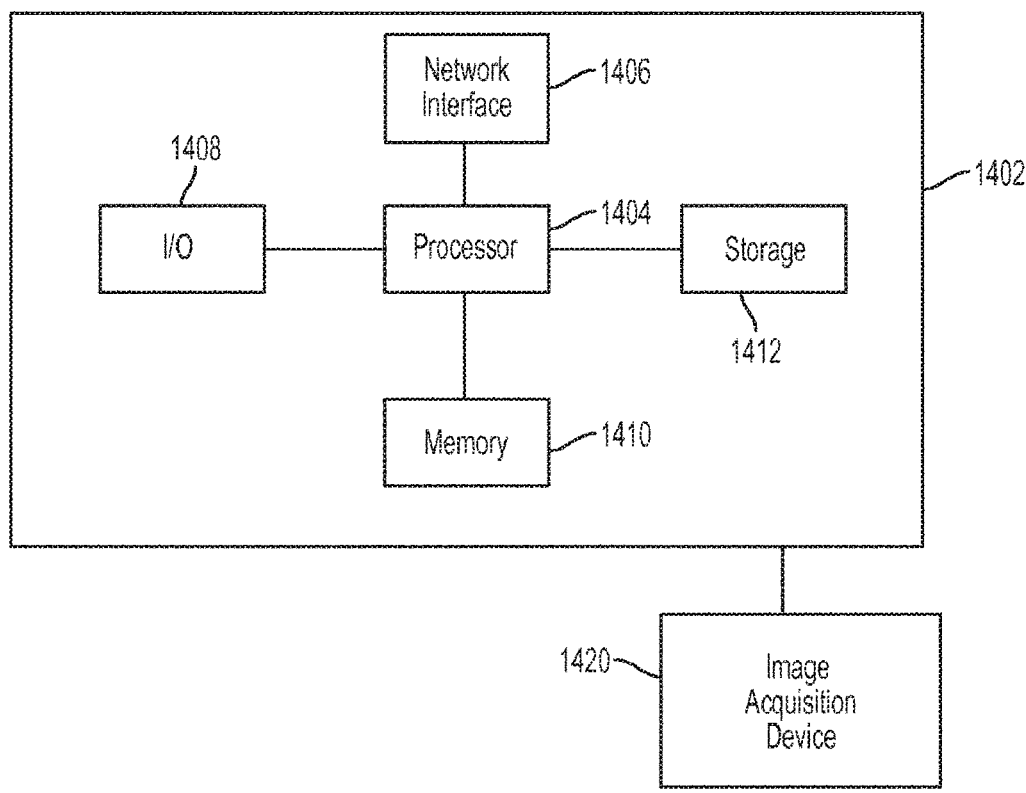
FIG. 14 is a high-level block diagram of a computer capable of implementing the present invention.

The above-described methods for training a machine-learning based mapping for determining FFR and determining FFR for a patient using a trained machine-learning based mapping can be implemented on a computer using well-known computer processors, memory units, storage devices, computer software, and other components. A high-level block diagram of such a computer is illustrated in FIG. 14. The scanner and workstation of FIGS. 7, 8, and 9 can be implemented using the computer of FIG. 14. Computer 1402 contains a processor 1404, which controls the overall operation of the computer 1402 by executing computer program instructions which define such operation. The computer program instructions may be stored in a storage device 1412 (e.g., magnetic disk) and loaded into memory 1410 when execution of the computer program instructions is desired. Thus, the steps of the methods of FIGS. 1, 4, 5, 6, 10, and 12 may be defined by the computer program instructions stored in the memory 1410 and/or storage 1412 and controlled by the processor 1404 executing the computer program instructions. An image acquisition device 1420, such as an MR scanning device, Ultrasound device, etc., can be connected to the computer 1402 to input image data to the computer 1402. It is possible to implement the image acquisition device 1420 and the computer 1402 as one device. It is also possible that the image acquisition device 1420 and the computer 1402 communicate wirelessly through a network. The computer 1402 also includes one or more network interfaces 1406 for communicating with other devices via a network. The computer 1402 also includes other input/output devices 1408 that enable user interaction with the computer 1402 (e.g., display, keyboard, mouse, speakers, buttons, etc.). Such input/output devices 1408 may be used in conjunction with a set of computer programs as an annotation tool to annotate volumes received from the image acquisition device 1420. One skilled in the art will recognize that an implementation of an actual computer could contain other components as well, and that FIG. 14 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for determining a rest state hemodynamic index for a stenosis of interest for a patient, comprising:
   receiving medical image data of the patient including the stenosis of interest;
   extracting a set of features for the stenosis of interest from the medical image data of the patient; and
   determining a value of a rest state hemodynamic index for the stenosis of interest based on the extracted set of features using a trained machine-learning based mapping, wherein the trained machine-learning based mapping is trained based on geometric features extracted from synthetically generated stenosis geometries and rest state a rest state hemodynamic index values corresponding to the synthetically generated stenosis geometries computed using computational fluid dynamics (CFD) simulations performed on the synthetically generated stenosis geometries.

2. The method of claim 1, wherein the trained machine-learning based mapping is an empirical learned model that combines features from the set of features with respective learned weights.

3. The method of claim 1, wherein the trained machine-learning based mapping is a regression function trained using image-based boosting ridge regression.

4. The method of claim 1, wherein extracting a set of features for the stenosis of interest from the medical image data of the patient comprises:
  extracting a plurality of features characterizing geometry of the stenosis of interest.

5. The method of claim 4, wherein the features characterizing the geometry of the stenosis of interest include proximal and distal reference diameters, minimal lumen diameter, lesion length.

6. The method of claim 5, wherein the features characterizing the geometry of the stenosis of interest further include entrance angle, entrance length, exit angle, exit length, percentage of diameter blocked by the stenosis, and percentage of the area blocked by the stenosis.

7. The method of claim 4, wherein extracting a set of features for the stenosis of interest from the medical image data of the patient further comprises:
  extracting one or more features characterizing morphology of the stenosis.

8. The method of claim 7, wherein the features characterizing morphology of the stenosis comprise binary parameters indicating presence or absence of one or more of calcification, plaque, thrombus, diffuse disease, total or sub-total occlusion, or myocardial bridging.

9. The method of claim 4, wherein extracting a set of features for the stenosis of interest from the medical image data of the patient further comprises:
  extracting one or more features characterizing geometry of a coronary artery branch in which the stenosis of interest is located.

10. The method of claim 4, wherein extracting a set of features for the stenosis of interest from the medical image data of the patient further comprises:
  extracting one or more features characterizing geometry of an entire coronary artery tree of the patient.

11. The method of claim 4, wherein extracting a set of features for the stenosis of interest from the medical image data of the patient further comprises:
  extracting one or more features characterizing coronary anatomy and function.

12. The method of claim 1, further comprising:
  receiving functional measurements of the patient;
  extracting one or more features from the functional measurements of the patient; and
  including the one or more features extracted from the functional measurements of the patient in the set of features used for determining the value of the rest state hemodynamic index.

13. The method of claim 1, further comprising:
  receiving demographic information of the patient;
  extracting one or more features from the demographic information of the patient; and
  including the one or more feature extracted from the demographic information of the patient in the set of features used for determining the value of the rest state hemodynamic index.

14. The method of claim 13, wherein the one or more features extracted from the demographic information comprise binary parameters indicating whether or not the patient has one or more of past history of heart disease, past history of valve dysfunction, or past history of valve repair or replacement.

15. The method of claim 4, wherein extracting a set of features for the stenosis of interest from the medical image data of the patient further comprises:
  extracting one or more features characterizing in-vitro blood tests.

16. The method of claim 1, further comprising:
  receiving a user input modifying one or more features in the set of features, resulting in a modified set of features reflecting a treatment scenario; and
  determining the value of the rest state hemodynamic index for the stenosis of interest based on the modified set of features using the trained machine-learning based mapping.

17. The method of claim 1, wherein the trained machine-learning based mapping is further trained based on rest state hemodynamic index values computed using a mechanistic model to simulate blood flow in a set of training data.

18. The method of claim 1, wherein the rest state hemodynamic index comprises one or more of pressure-drop, instantaneous wave-free ratio (IFR), or basal stenosis resistance (BSR).

19. An apparatus for determining a rest state hemodynamic index for a stenosis of interest for a patient, comprising:
  a processor; and
  a memory storing computer executable instructions, which when executed by the processor cause the processor to perform operations comprising:
  receiving medical image data of the patient including the stenosis of interest;
  extracting a set of features for the stenosis of interest from the medical image data of the patient; and
  determining a value of a rest state hemodynamic index for the stenosis of interest based on the extracted set of features using a trained machine-learning based mapping, wherein the trained machine-learning based mapping is trained based on geometric features extracted from synthetically generated stenosis geometries and rest state hemodynamic index values corresponding to the synthetically generated stenosis geometries computed using computational fluid dynamics (CFD) simulations performed on the synthetically generated stenosis geometries.

20. The apparatus of claim 19, wherein the trained machine-learning based mapping is a regression function trained using image-based boosting ridge regression.

21. The apparatus of claim 19, wherein extracting a set of features for the stenosis of interest from the medical image data of the patient comprises:
  extracting a plurality of features characterizing geometry of the stenosis of interest.

22. The apparatus of claim 21, wherein extracting a set of features for the stenosis of interest from the medical image data of the patient further comprises:
  extracting one or more features characterizing morphology of the stenosis.

23. The apparatus of claim 21, wherein extracting a set of features for the stenosis of interest from the medical image data of the patient further comprises:
  extracting one or more features characterizing geometry of a coronary artery branch in which the stenosis of interest is located; and
  extracting one or more features characterizing geometry of an entire coronary artery tree of the patient.

24. The apparatus of claim 19, wherein the rest state hemodynamic index comprises one or more of pressure-drop, instantaneous wave-free ratio (IFR), or basal stenosis resistance (BSR).

25. A non-transitory computer readable medium storing computer program instructions for determining a rest state hemodynamic index for a stenosis of interest for a patient, the computer program instructions when executed on a processor cause the processor to perform operations comprising:

receiving medical image data of the patient including the stenosis of interest;

extracting a set of features for the stenosis of interest from the medical image data of the patient; and determining a value of a rest state hemodynamic index for the stenosis of interest based on the extracted set of features using a trained machine-learning based mapping, wherein the trained machine-learning based mapping is trained based on geometric features extracted from synthetically generated stenosis geometries and rest state hemodynamic index values corresponding to the synthetically generated stenosis geometries computed using computational fluid dynamics (CFD) simulations performed on the synthetically generated stenosis geometries.

26. The non-transitory computer readable medium of claim 25, wherein the trained machine-learning based mapping is a regression function trained using image-based boosting ridge regression.

27. The non-transitory computer readable medium of claim 25, wherein extracting a set of features for the stenosis of interest from the medical image data of the patient comprises:

extracting a plurality of features characterizing geometry of the stenosis of interest.

28. The non-transitory computer readable medium of claim 27, wherein extracting a set of features for the stenosis of interest from the medical image data of the patient further comprises:

extracting one or more features characterizing morphology of the stenosis.

29. The non-transitory computer readable medium of claim 27, wherein extracting a set of features for the stenosis of interest from the medical image data of the patient further comprises:

extracting one or more features characterizing geometry of a coronary artery branch in which the stenosis of interest is located; and extracting one or more features characterizing geometry of an entire coronary artery tree of the patient.

30. The non-transitory computer readable medium of claim 25, wherein the rest state hemodynamic index comprises one or more of pressure-drop, instantaneous wave-free ratio (IFR), or basal stenosis resistance (BSR).

* * * * *